US 7,100,530 B2

(12) United States Patent
Lu

(10) Patent No.: US 7,100,530 B2
(45) Date of Patent: Sep. 5, 2006

(54) DOSE INDICATING DEVICE

(75) Inventor: Winston Z. Lu, Kitchener (CA)

(73) Assignee: Trudell Medical International, Inc., London (CA)

( * ) Notice: Subject to any disclaimer, the term of this patent is extended or adjusted under 35 U.S.C. 154(b) by 58 days.

(21) Appl. No.: 10/869,363

(22) Filed: Jun. 16, 2004

(65) Prior Publication Data

US 2005/0126469 A1 Jun. 16, 2005

Related U.S. Application Data

(60) Provisional application No. 60/529,659, filed on Dec. 15, 2003.

(51) Int. Cl.
*G09F 9/00* (2006.01)
(52) U.S. Cl. .................. 116/307; 116/309; 116/312; 116/313; 116/284; 128/200.23; 128/205.23
(58) Field of Classification Search ............. 116/307, 116/306, 309, 311, 312, 313, 316, 317, 284, 116/299; 235/453; 128/200.23, 203.15, 128/205.2; 222/30, 38, 23, 36
See application file for complete search history.

(56) References Cited

U.S. PATENT DOCUMENTS 165,054 A 6/1875 Baldwin (Continued)

FOREIGN PATENT DOCUMENTS

AU 598250 B2 6/1990

(Continued)

OTHER PUBLICATIONS

International Search Report in International Application No. PCT/IB03/01032, dated Aug. 19, 2003, 10 pages.

(Continued)

*Primary Examiner*—Diego Gutierrez
*Assistant Examiner*—Travis Reis
(74) *Attorney, Agent, or Firm*—Brinks Hofer Gilson & Lione

(57) ABSTRACT

An indicating device suitable for indicating the number of metered dosages that have been dispensed from or remain in a container includes a base member adapted to be mounted to the container and a cap member moveably connected to the base member. The cap member is moveable relative to the base member along an axial path. A shaft is non-rotatably mounted to one of the cap member and the base member and defines an axis. An indicator member is rotatably mounted on the shaft and is rotatable in at least a first direction. One of the shaft and the indicator member has a helical groove while the other of the shaft and the indicator member has a follower disposed in the groove. The indicator member is moveable relative to the shaft along the axis as the indicator member is rotated in the first direction. In another embodiment, the indicating device includes first, second and third indicator members. In yet another embodiment, the indicating device includes a housing having a longitudinally extending cavity shaped to receive the container and an indicator member disposed in the cavity and having a longitudinally extending wall shaped to surround at least a portion of the container. The indicator member is rotatably mounted within the housing and is rotatable relative thereto about a longitudinal axis. The indicator member includes a driven gear. A drive gear is disposed in the housing and includes a drive portion selectively engaged with the driven gear. An actuator is adapted to move with the container and is selectively engaged with the drive gear.

22 Claims, 9 Drawing Sheets

U.S. PATENT DOCUMENTS

| | | |
|---|---|---|
| 498,851 A | 6/1893 | Jones |
| 1,219,858 A | 3/1917 | Patterson |
| 2,455,962 A | 12/1948 | Wheeler et al. |
| 2,580,292 A | 12/1951 | Geary et al. |
| 2,587,147 A | 2/1952 | Guion et al. |
| 2,630,027 A | 3/1953 | Wunderlich |
| 2,644,452 A | 7/1953 | Brown |
| 2,767,680 A | 10/1956 | Lermer |
| 2,770,711 A | 11/1956 | Baranowski |
| 2,841,190 A | 7/1958 | Scheck |
| 2,883,086 A | 4/1959 | Davison et al. |
| 2,939,597 A | 6/1960 | Greene |
| 2,943,730 A | 7/1960 | Tregilgas |
| 2,953,242 A | 9/1960 | Shaw |
| 3,001,524 A | 9/1961 | Maison et al. |
| 3,073,468 A | 1/1963 | Arneson |
| 3,085,745 A | 4/1963 | Auberger |
| 3,119,557 A | 1/1964 | Chapman |
| 3,120,318 A | 2/1964 | Rigor |
| 3,148,801 A | 9/1964 | Radeloff et al. |
| 3,151,599 A | 10/1964 | Livingston |
| 3,170,597 A | 2/1965 | Reichenberger |
| 3,187,963 A | 6/1965 | Anderson |
| 3,189,232 A | 6/1965 | Joffe |
| 3,191,867 A | 6/1965 | Helms |
| 3,240,389 A | 3/1966 | Genua |
| 3,334,731 A | 8/1967 | Dale |
| 3,344,951 A | 10/1967 | Gervais |
| 3,361,306 A | 1/1968 | Grim |
| 3,402,863 A | 9/1968 | Green |
| 3,419,187 A | 12/1968 | Bazarnic |
| 3,446,179 A | 5/1969 | Bender |
| 3,477,561 A | 11/1969 | Espinal |
| 3,495,567 A | 2/1970 | Hayes et al. |
| 3,511,409 A | 5/1970 | Huck |
| 3,549,057 A | 12/1970 | Perez |
| 3,568,629 A * | 3/1971 | Porter ................ 116/231 |
| 3,572,282 A | 3/1971 | Trump et al. |
| 3,589,563 A | 6/1971 | Carragan et al. |
| 3,612,349 A | 10/1971 | Thomas |
| 3,654,890 A * | 4/1972 | Rigney et al. ............. 116/308 |
| 3,655,952 A | 4/1972 | Johnson et al. |
| 3,688,945 A | 9/1972 | Harman, Jr. et al. |
| 3,753,417 A | 8/1973 | Garby |
| 3,766,882 A | 10/1973 | Babbitt, III |
| 3,789,843 A | 2/1974 | Armstrong et al. |
| 3,792,242 A | 2/1974 | Hanson |
| 3,796,348 A | 3/1974 | Zipper |
| 3,797,748 A | 3/1974 | Nozawa, et al. |
| 3,802,608 A | 4/1974 | Gullett |
| 3,831,808 A | 8/1974 | Bender |
| 3,831,812 A | 8/1974 | Dolan |
| 3,845,883 A | 11/1974 | Johnson et al. |
| 3,848,774 A | 11/1974 | Schimke |
| 3,886,879 A | 6/1975 | Frost et al. |
| 3,887,099 A | 6/1975 | Gillman et al. |
| 3,921,568 A | 11/1975 | Fish |
| 3,926,326 A | 12/1975 | Grau |
| 3,950,939 A | 4/1976 | Meisner et al. |
| 3,960,713 A | 6/1976 | Carey |
| 3,977,554 A | 8/1976 | Costa |
| 3,994,421 A | 11/1976 | Hansen |
| 4,011,829 A | 3/1977 | Wachsmann et al. |
| 4,029,033 A | 6/1977 | Kerwin et al. |
| 4,034,757 A | 7/1977 | Glover |
| 4,037,719 A | 7/1977 | Perlmutter |
| 4,069,935 A | 1/1978 | Hampel |
| 4,069,942 A | 1/1978 | Marshall et al. |
| 4,078,661 A | 3/1978 | Thomas |
| 4,094,408 A | 6/1978 | Ford |
| 4,162,746 A | 7/1979 | Anderson et al. |
| 4,164,301 A | 8/1979 | Thayer |
| 4,188,984 A | 2/1980 | Lyall |
| 4,220,247 A | 9/1980 | Kramer |
| 4,291,688 A | 9/1981 | Kistler |
| 4,300,548 A | 11/1981 | Jones |
| 4,319,128 A | 3/1982 | Dow, Jr. et al. |
| 4,345,541 A | 8/1982 | Villa-Real |
| 4,347,804 A | 9/1982 | Villa-Real |
| 4,347,853 A | 9/1982 | Gereg et al. |
| 4,350,265 A | 9/1982 | Griffiths et al. |
| 4,354,621 A | 10/1982 | Knickerbocker |
| 4,357,192 A | 11/1982 | Moser |
| 4,365,722 A | 12/1982 | Kramer |
| 4,368,381 A | 1/1983 | Ishiyama |
| 4,405,045 A | 9/1983 | Villa-Real |
| 4,419,016 A | 12/1983 | Zoltan |
| 4,432,300 A | 2/1984 | Lyss |
| 4,436,223 A | 3/1984 | Wilson |
| 4,440,306 A | 4/1984 | Van Buskirk et al. |
| 4,489,834 A | 12/1984 | Thackrey |
| 4,500,005 A | 2/1985 | Forrester |
| 4,501,370 A | 2/1985 | Kelley |
| 4,511,150 A | 4/1985 | Seguenot |
| 4,523,933 A | 6/1985 | Laush et al. |
| 4,528,933 A | 7/1985 | Allen |
| 4,534,345 A | 8/1985 | Wetterlin |
| 4,538,744 A | 9/1985 | Weissenborn |
| 4,548,157 A | 10/1985 | Hevoyan |
| 4,562,933 A | 1/1986 | Dennis |
| 4,565,302 A | 1/1986 | Pfeiffer et al. |
| 4,599,508 A | 7/1986 | Smetaniuk |
| 4,634,012 A | 1/1987 | Kelley |
| 4,637,528 A | 1/1987 | Wachinski et al. |
| 4,641,759 A | 2/1987 | Kelley |
| 4,646,936 A | 3/1987 | Frazier et al. |
| 4,662,520 A | 5/1987 | Griffin |
| 4,664,107 A | 5/1987 | Wass |
| 4,666,051 A | 5/1987 | Trick |
| 4,668,218 A | 5/1987 | Virtanen |
| 4,677,975 A | 7/1987 | Edgar et al. |
| 4,693,399 A | 9/1987 | Hickman et al. |
| 4,705,182 A | 11/1987 | Newel-Lewis |
| 4,722,729 A | 2/1988 | Dettbarn et al. |
| 4,723,673 A | 2/1988 | Tartaglia et al. |
| 4,727,886 A | 3/1988 | Conrardy et al. |
| 4,736,871 A | 4/1988 | Luciani et al. |
| 4,749,093 A | 6/1988 | Trick |
| 4,753,189 A | 6/1988 | Mastman et al. |
| 4,756,423 A | 7/1988 | Holtsch |
| 4,782,966 A | 11/1988 | Thackrey |
| 4,792,664 A | 12/1988 | Schwab |
| 4,817,822 A | 4/1989 | Rand et al. |
| 4,890,572 A | 1/1990 | Huang |
| 4,934,358 A | 6/1990 | Nilsson et al. |
| 4,947,875 A | 8/1990 | Brooks et al. |
| 4,955,371 A | 9/1990 | Zamba et al. |
| 4,969,578 A | 11/1990 | Gander et al. |
| 4,984,158 A | 1/1991 | Hillsman |
| 5,009,338 A | 4/1991 | Barker |
| 5,011,032 A | 4/1991 | Rollman |
| 5,020,527 A | 6/1991 | Dessertine |
| 5,027,806 A | 7/1991 | Zoltan et al. |
| 5,027,808 A | 7/1991 | Rich et al. |
| 5,038,972 A | 8/1991 | Muderlak et al. |
| 5,060,643 A | 10/1991 | Rich et al. |
| 5,069,204 A | 12/1991 | Smith et al. |
| 5,082,129 A | 1/1992 | Kramer |
| 5,082,130 A | 1/1992 | Weinstein |
| 5,115,929 A | 5/1992 | Buono |
| 5,174,473 A | 12/1992 | Marelli |
| 5,184,761 A | 2/1993 | Lee |
| 5,188,251 A | 2/1993 | Kusz |
| 5,190,643 A | 3/1993 | Duncan et al. |

| | | | | | | |
|---|---|---|---|---|---|---|
| 5,209,375 | A | 5/1993 | Fuchs | 5,896,855 | A | 4/1999 | Hobbs et al. |
| 5,217,004 | A | 6/1993 | Blasnik et al. | 5,896,990 | A * | 4/1999 | Barzana ............... 116/309 |
| 5,224,474 | A | 7/1993 | Bloomfield | 5,899,201 | A | 5/1999 | Schultz et al. |
| 5,227,764 | A | 7/1993 | Umemoto | 5,904,139 | A | 5/1999 | Hauser |
| 5,228,586 | A | 7/1993 | Fuchs | 5,957,896 | A | 9/1999 | Bendek et al. |
| 5,242,067 | A | 9/1993 | Garby et al. | 5,988,496 | A | 11/1999 | Bruna |
| 5,243,970 | A | 9/1993 | Ambrosio et al. | 6,000,159 | A * | 12/1999 | Hornung ............... 116/309 |
| 5,261,548 | A | 11/1993 | Barker et al. | 6,012,450 | A | 1/2000 | Rubsamen |
| 5,263,475 | A | 11/1993 | Altermatt et al. | 6,029,659 | A | 2/2000 | O'Connor |
| 5,284,133 | A | 2/1994 | Burns et al. | 6,059,133 | A * | 5/2000 | Lai ........................ 116/309 |
| 5,289,946 | A | 3/1994 | Fuchs | 6,062,214 | A | 5/2000 | Howlett |
| 5,299,701 | A | 4/1994 | Barker et al. | 6,076,521 | A | 6/2000 | Lindahl et al. |
| 5,300,042 | A | 4/1994 | Kossoff et al. | 6,082,358 | A | 7/2000 | Scarrott et al. |
| 5,301,873 | A | 4/1994 | Burke et al. | 6,089,180 | A * | 7/2000 | Nichols, Jr. ............ 116/309 |
| 5,328,597 | A | 7/1994 | Boldt, Jr. et al. | 6,119,684 | A | 9/2000 | Nohl et al. |
| 5,331,953 | A | 7/1994 | Andersson et al. | 6,138,669 | A | 10/2000 | Rocci, Jr. et al. |
| 5,335,823 | A | 8/1994 | Fuchs et al. | 6,142,339 | A | 11/2000 | Blacker et al. |
| 5,349,944 | A | 9/1994 | Chippendale et al. | 6,148,815 | A | 11/2000 | Wolf |
| 5,349,945 | A | 9/1994 | Wass et al. | 6,149,054 | A | 11/2000 | Cirrillo |
| 5,356,012 | A | 10/1994 | Tang et al. | 6,161,724 | A | 12/2000 | Blacker et al. |
| 5,363,842 | A | 11/1994 | Mishelevich et al. | 6,164,494 | A | 12/2000 | Marelli |
| 5,370,267 | A | 12/1994 | Schroeder | 6,202,642 | B1 | 3/2001 | McKinnon et al. |
| 5,382,243 | A | 1/1995 | Mulholland | 6,223,744 | B1 | 5/2001 | Garon |
| RE34,847 | E | 2/1995 | Muderlak et al. | 6,234,168 | B1 | 5/2001 | Bruna |
| 5,388,572 | A | 2/1995 | Mulhauser et al. | 6,283,365 | B1 | 9/2001 | Bason |
| 5,392,768 | A | 2/1995 | Johansson et al. | 6,328,037 | B1 | 12/2001 | Scarrott et al. |
| 5,394,866 | A | 3/1995 | Ritson et al. | 6,336,453 | B1 | 1/2002 | Scarrott et al. |
| 5,397,028 | A | 3/1995 | Jesadanont | 6,360,739 | B1 | 3/2002 | Rand et al. |
| 5,411,173 | A | 5/1995 | Weinstein | 6,405,727 | B1 | 6/2002 | MacMichael et al. |
| 5,421,482 | A | 6/1995 | Garby et al. | 6,415,785 | B1 | 7/2002 | Stage |
| 5,437,270 | A | 8/1995 | Braithwaite | 6,425,392 | B1 | 7/2002 | Sosiak |
| 5,447,150 | A | 9/1995 | Bacon | 6,431,168 | B1 | 8/2002 | Rand et al. |
| 5,448,042 | A | 9/1995 | Robinson et al. | 6,435,372 | B1 | 8/2002 | Blacker et al. |
| 5,482,030 | A | 1/1996 | Klein | 6,446,627 | B1 | 9/2002 | Bowman et al. |
| 5,482,163 | A * | 1/1996 | Hoffman ............... 116/309 | 6,474,331 | B1 | 11/2002 | Rand et al. |
| 5,505,192 | A | 4/1996 | Samiotes et al. | 6,481,438 | B1 | 11/2002 | Gallem et al. |
| 5,505,195 | A | 4/1996 | Wolf et al. | 6,484,717 | B1 | 11/2002 | Dagsland et al. |
| 5,509,905 | A | 4/1996 | Michel | 6,516,799 | B1 | 2/2003 | Greenwood et al. |
| 5,519,197 | A | 5/1996 | Robinson et al. | 6,529,446 | B1 | 3/2003 | de la Huerga |
| 5,520,166 | A | 5/1996 | Ritson et al. | 6,561,384 | B1 | 5/2003 | Blacker et al. |
| 5,522,378 | A | 6/1996 | Ritson et al. | 6,601,582 | B1 | 8/2003 | Rand et al. |
| 5,544,647 | A | 8/1996 | Jewett et al. | 6,615,827 | B1 | 9/2003 | Greenwood et al. |
| 5,549,101 | A | 8/1996 | Trofast et al. | 6,659,307 | B1 | 12/2003 | Stradella |
| 5,564,414 | A | 10/1996 | Walker et al. | 6,679,251 | B1 | 1/2004 | Gallem et al. |
| 5,574,268 | A * | 11/1996 | Herman et al. ........... 116/316 | 6,701,917 | B1 | 3/2004 | O'Leary |
| 5,611,444 | A | 3/1997 | Garby et al. | 6,718,972 | B1 * | 4/2004 | O'Leary ............. 128/203.15 |
| 5,617,844 | A | 4/1997 | King | 6,729,330 | B1 | 5/2004 | Scarrott et al. |
| 5,622,163 | A | 4/1997 | Jewett et al. | 6,752,153 | B1 | 6/2004 | Eckert |
| 5,625,334 | A | 4/1997 | Compton | 6,761,161 | B1 | 7/2004 | Scarrott et al. |
| 5,625,659 | A | 4/1997 | Sears | 6,766,799 | B1 | 7/2004 | Edwards et al. |
| 5,638,970 | A | 6/1997 | Garby et al. | 6,907,876 | B1 | 6/2005 | Clark et al. |
| 5,657,748 | A | 8/1997 | Braithwaite | 2002/0153005 | A1 | 10/2002 | Scarrott et al. |
| 5,676,129 | A | 10/1997 | Rocci, Jr. et al. | 2003/0183225 | A1* | 10/2003 | Knudsen ............. 128/200.23 |
| 5,687,710 | A | 11/1997 | Ambrosio et al. | 2003/0200996 | A1 | 10/2003 | Blakley et al. |
| 5,692,492 | A | 12/1997 | Bruna et al. | 2003/0209239 | A1 | 11/2003 | Rand et al. |
| 5,694,882 | A | 12/1997 | Marshall | 2004/0069301 | A1 | 4/2004 | Bacon |
| 5,718,355 | A | 2/1998 | Garby et al. | 2004/0144798 | A1 | 7/2004 | Ouyang et al. |
| 5,724,957 | A | 3/1998 | Rubsamen et al. | 2004/0149772 | A1 | 8/2004 | Ouyang |
| 5,732,836 | A | 3/1998 | Barker et al. | 2004/0149773 | A1 | 8/2004 | Ouyang et al. |
| 5,740,792 | A | 4/1998 | Ashley et al. | 2004/0221840 | A1 | 11/2004 | Stockman-Lamb |
| 5,758,638 | A | 6/1998 | Kreamer | 2004/0255935 | A1 | 12/2004 | Bruna |
| 5,772,074 | A | 6/1998 | Dial et al. | 2004/0255936 | A1 | 12/2004 | Urbanus |
| 5,794,612 | A | 8/1998 | Wachter et al. | 2005/0011515 | A1 | 1/2005 | Lee et al. |
| 5,799,651 | A | 9/1998 | Garby et al. | | | | |
| 5,803,283 | A | 9/1998 | Barker et al. | | | | |
| 5,809,997 | A | 9/1998 | Wolf | | | | |

FOREIGN PATENT DOCUMENTS

| | | |
|---|---|---|
| 5,826,571 A | 10/1998 Casper et al. | CA 535518 1/1957 |
| 5,829,434 A | 11/1998 Ambrosio et al. | DE 6 603 758 7/1969 |
| 5,845,777 A * | 12/1998 Najmi ............... 116/317 | DE 27 02 539 A1 1/1977 |
| 5,852,590 A | 12/1998 de la Huerga | DE 3336486 A1 4/1984 |
| 5,871,007 A | 2/1999 Clark, Jr. | DE 8 590 143.1 10/1985 |
| 5,873,995 A | 2/1999 Huang et al. | DE 86 02 238.5 5/1986 |
| 5,882,507 A | 3/1999 Tanner et al. | EP 0 028 929 A2 5/1981 |

| | | |
|---|---|---|
| EP | 0 098 939 A2 | 1/1984 |
| EP | 0 114 617 A2 | 8/1984 |
| EP | 0 063 599 | 6/1986 |
| EP | 0 230 323 B1 | 7/1987 |
| EP | 0 236 871 A2 | 9/1987 |
| EP | 0 269 496 A2 | 6/1988 |
| EP | 0 280 104 B1 | 8/1988 |
| EP | 0 488 609 A1 | 6/1992 |
| EP | 0 559 757 B1 | 9/1993 |
| EP | 0 949 584 A2 | 10/1999 |
| EP | 0 949 584 A3 | 9/2001 |
| EP | 1 220 802 B1 | 2/2004 |
| FR | 2 743 055 A1 | 7/1997 |
| GB | 998148 | 7/1965 |
| GB | 1058636 | 2/1967 |
| GB | 1 290 484 | 9/1972 |
| GB | 1317315 | 5/1973 |
| GB | 2 036 695 A | 7/1980 |
| GB | 2 063 075 A | 6/1981 |
| GB | 2 092 991 A | 8/1982 |
| GB | 2 104 393 A | 3/1983 |
| GB | 2 191 032 A | 12/1987 |
| GB | 2 195 544 A | 4/1988 |
| GB | 2 348 928 A | 10/2000 |
| WO | WO 86/02275 | 4/1986 |
| WO | WO 87/04354 | 8/1987 |
| WO | WO 90/10470 | 9/1990 |
| WO | WO 91/06334 | 5/1991 |
| WO | WO 92/07600 | 5/1992 |
| WO | WO 92/09324 | 6/1992 |
| WO | WO 92/15353 | 9/1992 |
| WO | WO 92/17231 | 10/1992 |
| WO | WO 93/24167 | 12/1993 |
| WO | WO 94/11272 | 5/1994 |
| WO | WO 94/14492 | 7/1994 |
| WO | WO 95/34874 | 12/1995 |
| WO | WO 96/16686 | 6/1996 |
| WO | WO 96/16687 | 6/1996 |
| WO | WO 96/39337 | 12/1996 |
| WO | WO 98/01822 | 1/1998 |
| WO | WO 98/56444 | 12/1998 |
| WO | WO 98/56445 | 12/1998 |
| WO | WO 99/36115 | 7/1999 |
| WO | WO 99/57019 | 11/1999 |
| WO | WO 00/09187 | 2/2000 |
| WO | WO 00/59806 | 10/2000 |
| WO | WO 01/28887 A1 | 4/2001 |
| WO | WO 01/29765 | 4/2001 |
| WO | WO 01/37909 A1 | 5/2001 |
| WO | WO 03/103759 A1 | 12/2003 |
| WO | WO 03/1015141 A1 | 12/2003 |
| WO | WO 2004/089451 A1 | 10/2004 |

OTHER PUBLICATIONS

International Search Report, PCT/IB2004/004062, Apr. 6, 2005.

* cited by examiner

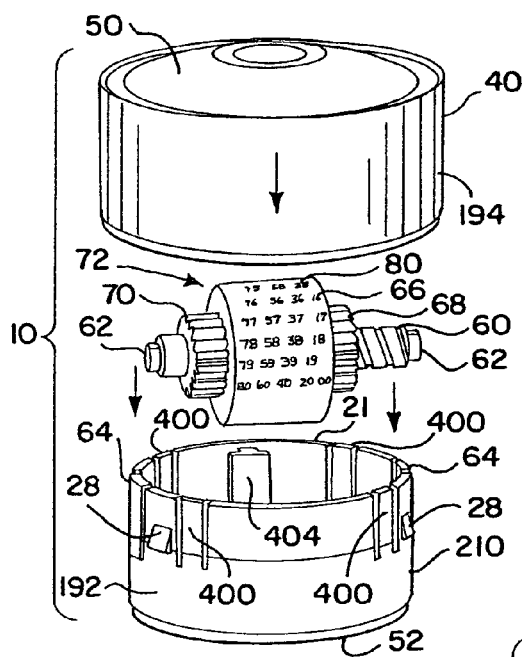
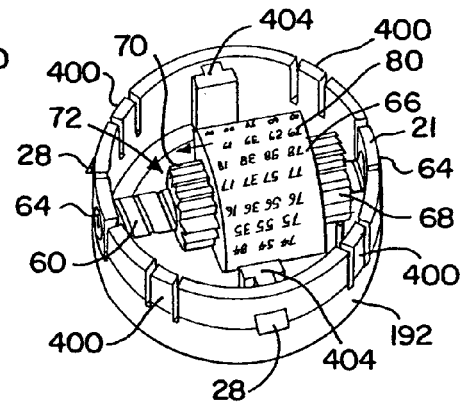
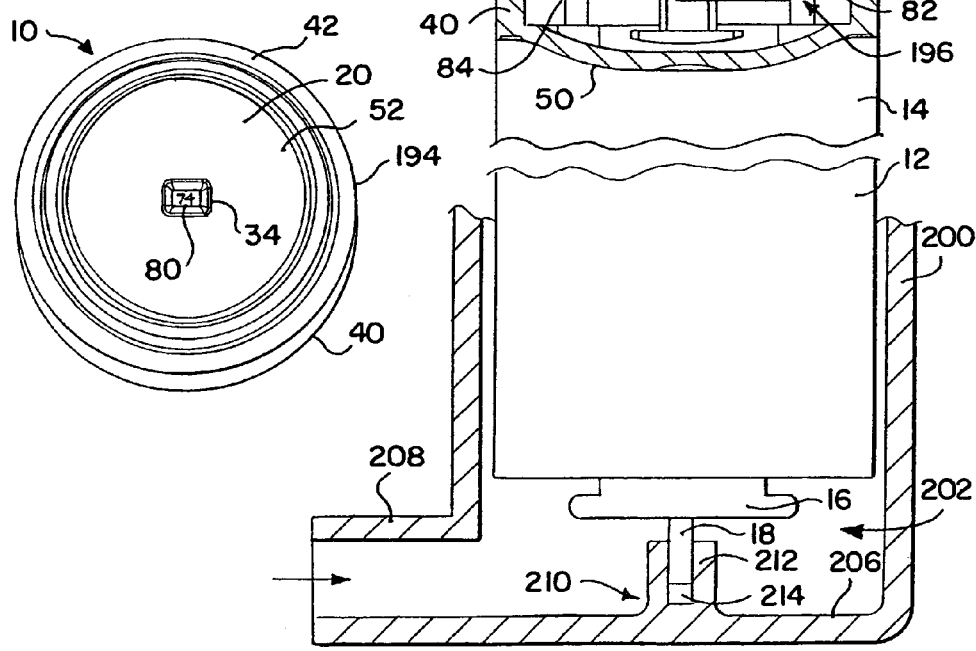

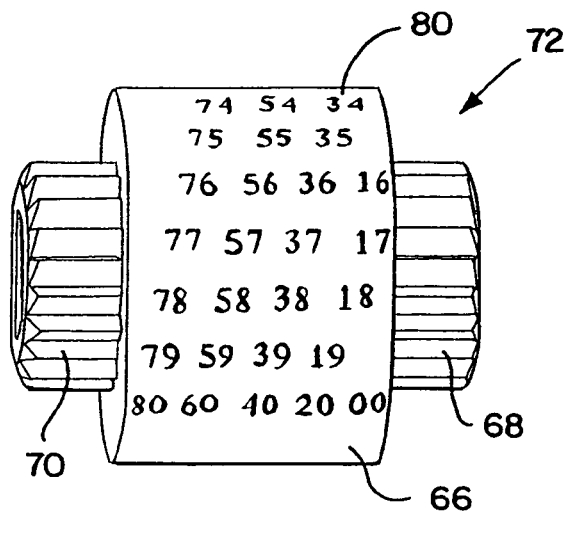
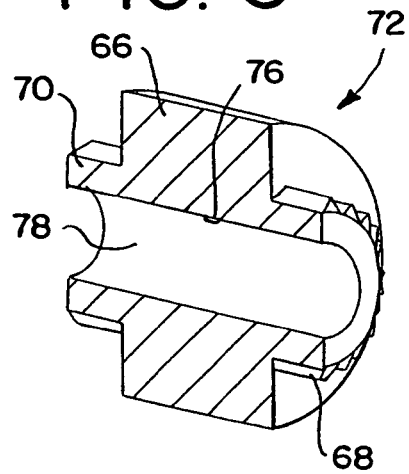
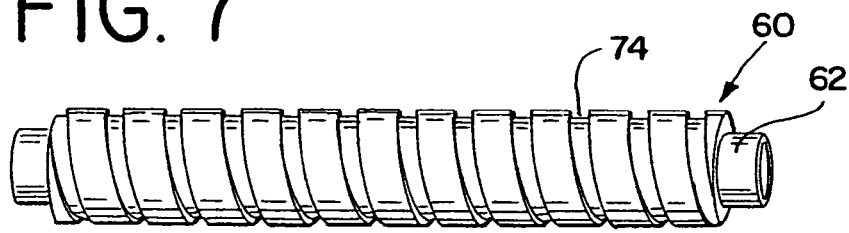
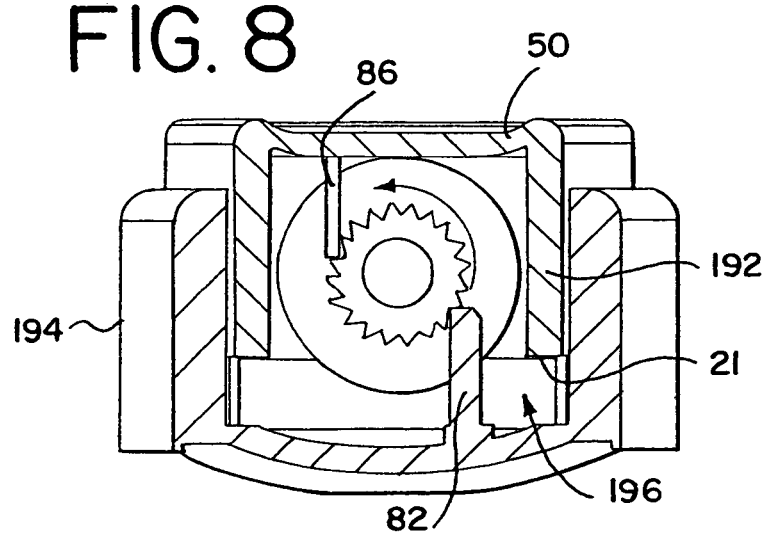

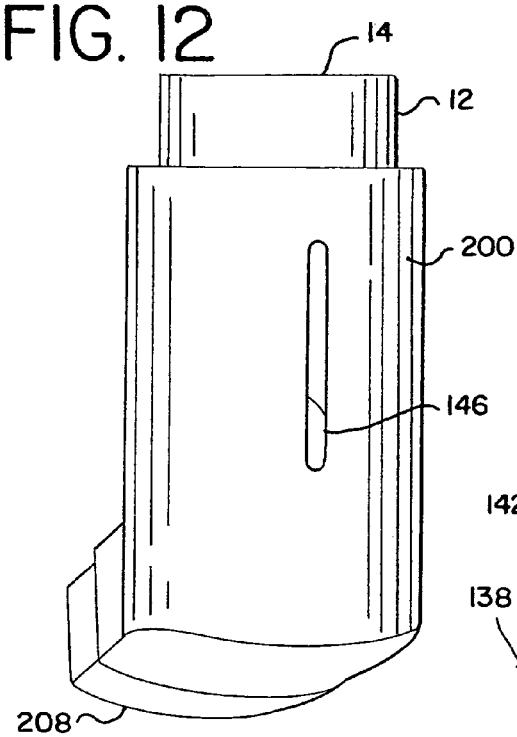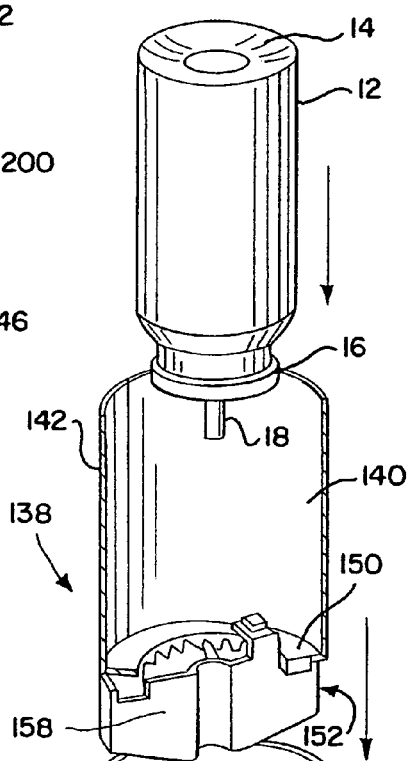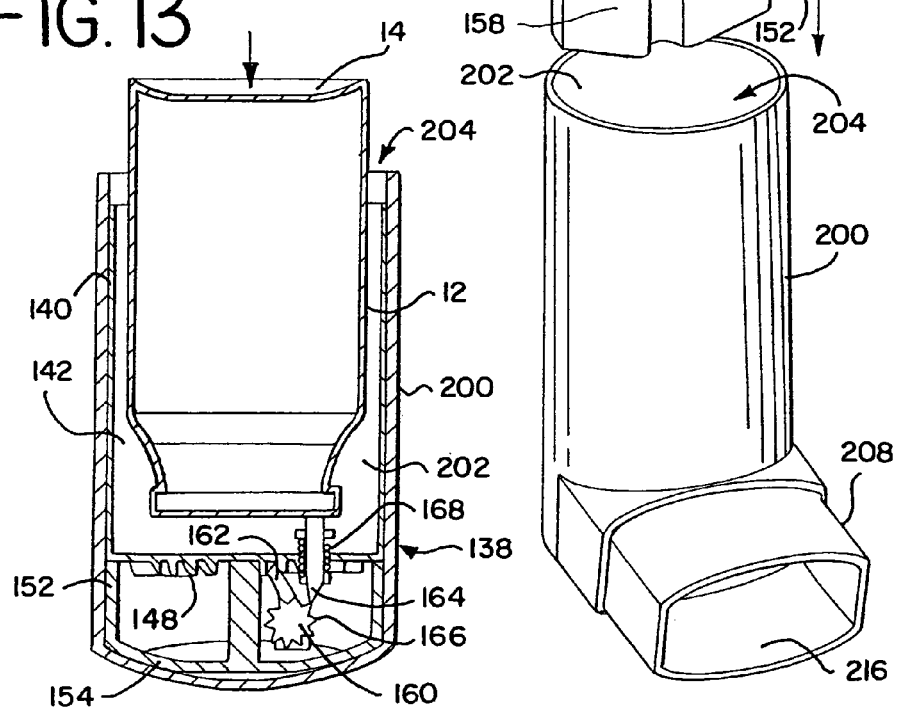

DOSE INDICATING DEVICE

This application claims the benefit of U.S. Provisional Patent Application Ser. No. 60/529,659, filed Dec. 15, 2003, the entire disclosure of which is hereby incorporated herein by reference.

BACKGROUND

The present invention relates generally to an indicating device for indicating the number of dosages that have been dispensed from or remain in a container.

Aerosol dispensing devices have been developed that include a dose indicating device to indicate the number of metered doses that have been dispensed from the device, or to indicate the number of doses remaining therein. For example, patients have certain conditions that can be treated with medicaments dispensed in an aerosol and administered to the patient by inhalation. In one format, the aerosol with medicaments are contained in a container, and dispensed in metered, or measured, dosages with an inhalation device, or actuator boot. In such an arrangement, it can be important for the patient to be able to ascertain the number of metered doses remaining in the container, either by an indication of the number remaining therein or by knowledge of the number already dispensed therefrom, such that the patient is not caught unaware with an empty container when in need of the medicament. Thus, it may be important for the inhalation device to provide an accurate indication of either the number of doses remaining in the container, or the number of doses already dispensed therefrom.

Typically, a conventional aerosol container includes a body and a valve stem that can be depressed relative to the body so as to emit the metered dose of aerosol and medicament. The container typically is supplied with a predetermined number of metered doses, generally on the order of about 200, such that the counting of the number of valve stem depressions, and corresponding number of dispensed metered doses, can be directly correlated with the number of doses remaining in the container.

In operation, the container is typically received within a housing of the inhalation device, wherein the valve is brought into engagement with a support block in the housing. The user administers the medicament by moving the container relative to the housing so as to depress the valve stem and internal valve and thereby release a metered dose, which is typically administered to the user through a port or mouthpiece extending from the housing. After the dose is administered, the valve stem, which is typically spring loaded, biases the container away from the support block so as to again move the container relative to the housing. In this way, a metered dose of medicament is administered by each cycle of linear reciprocal movement of the container relative to the housing.

Some actuator boots, or other devices attached to the medicament container, have indicating devices that convert the linear reciprocal movement of the container relative to the housing into a one-way, or single-cycle, movement of an indicator, wherein the indicator identifies the relative fullness of the container, the number of metered doses remaining therein or the number of doses already administered.

SUMMARY

Briefly stated, in one preferred embodiment, an indicating device suitable for indicating the number of metered dosages that have been dispensed from or remain in a container includes a base member adapted to be mounted to the container and a cap member moveably connected to the base member. The cap member is moveable relative to the base member along an axial path. A shaft is mounted to one of the cap member and the base member and defines an axis. An indicator member is rotatably mounted on the shaft and is rotatable about the shaft in at least a first direction. One of the shaft and the indicator member has a helical groove while the other of the shaft and the indicator member has a follower disposed in the groove. The indicator member is moveable relative to the shaft along the axis as the indicator member is rotated in the first direction.

In another embodiment, an indicating device includes a housing having a longitudinally extending cavity shaped to receive the container and an indicator member disposed in the cavity and having a longitudinally extending wall shaped to surround at least a portion of the container. The indicator member is rotatably mounted within the housing and is rotatable relative thereto about a longitudinal axis. The indicator member includes a driven gear. A drive gear is disposed in the housing and includes a drive portion selectively engaged with the driven gear. An actuator is adapted to move with the container and is selectively engaged with the drive gear.

In yet another embodiment, an indicating device includes a base member adapted to be mounted to the container and a cap member moveably connected to the base member. The cap member is moveable relative to the base member along an axial path. A first indicator member includes first primary dosage indicia and a second indicator member includes second primary dosage indicia, wherein the first and second primary dosage indicia are adapted to indicate the number of dosages of substance that have been dispensed from or remain in the container. The first indicator member includes a plurality of first driven teeth and a plurality of driving teeth. The second indicator member includes a first advancement member selectively engaged with at least one of the plurality of the first driven teeth. A third indicator member includes secondary dosage indicia which are adapted to indicate that less than a minimum predetermined number of dosages of substance remain in the container. The third indicator member includes a plurality of second driven teeth. The first, second and third indicator members are rotatably mounted in one of the cap member and the base member, which includes a first engagement member selectively engaged with and biasing at least one of the plurality of second driven teeth into engagement with at least one of the plurality of the driving teeth on the first indicator member. One of the cap member and base member includes a second engagement member selectively engaged with and biasing the first advancement member into selective engagement with the at least one of the plurality of first driven teeth.

Methods for indicating the number of metered dosages of substance dispensed from or remaining in the container using the various embodiments are also provided.

The various embodiments provide simple, robust and inexpensive solutions for providing the user with information allowing them to ascertain the number of metered doses remaining in the container, either by an indication of the number remaining therein or by knowledge of the number already dispensed therefrom.

The foregoing paragraphs have been provided by way of general introduction, and are not intended to limit the scope of the following claims. The various preferred embodiments, together with further advantages, will be best understood by reference to the following detailed description taken in conjunction with the accompanying drawings.

BRIEF DESCRIPTION OF THE DRAWINGS

FIG. 1 is an exploded side perspective view of a first embodiment of a dose indicating device.

FIG. 2 is a top perspective view of the dose indicating device shown in FIG. 1.

FIG. 3 is a bottom perspective view of a cap member with an indicator mounted thereto.

FIG. 4 is a side, cross-sectional view of the dose indicating device shown in FIG. 1 taken along the axis of a shaft, with the dose indicating device mounted on a disposed in an actuator boot.

FIG. 5 is an enlarged perspective view of an indicator member.

FIG. 6 is a partial, perspective view of the indicator member shown in FIG. 5.

FIG. 7 is a perspective view of a shaft having a helical groove.

FIG. 8 is a side, cross-sectional view of the dose indicating device shown in FIG. 1 taken substantially perpendicular to the axis of the shaft.

FIG. 12 is a perspective view of an actuator boot and container, with a second embodiment of a dose indicating device disposed in the actuator boot.

FIG. 13 is a cross-sectional view of the container, actuator boot and dose indicating device shown in FIG. 12.

FIG. 14 is an exploded perspective view of the container, actuator boot and dose indicating device shown in FIG. 12.

FIG. 31 is a perspective view of one embodiment of a base member.

DETAILED DESCRIPTION OF THE PRESENTLY PREFERRED EMBODIMENTS

Figure 9:
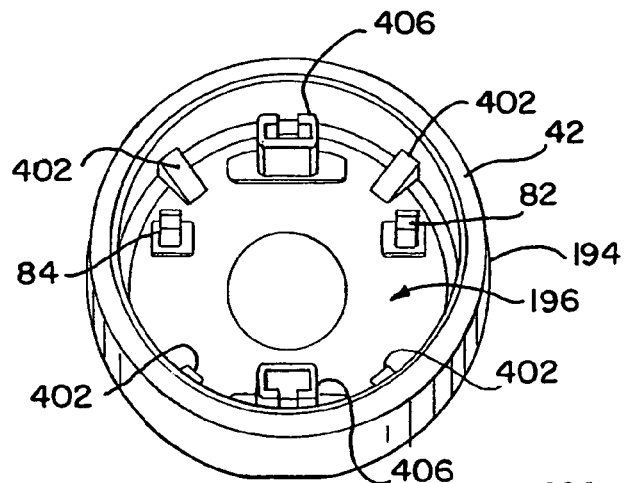
FIG. 9 is a top perspective view of a base member.

General Description of Dispenser:

Referring to the drawings, and in particular FIGS. 4, 12–14, 34 and 36, an aerosol dispenser is shown as including a housing 200, or actuator boot, and a container 12 disposed therein. The housing has a longitudinally extending cavity 202 shaped to receive the container. A top portion of the housing is generally open such that the container can be inserted in the housing through an opening 204 and installed therein with a bottom end 14 of the container protruding from the housing so as to be exposed to the user for actuation.

The terms "longitudinal" and "axial" as used herein are intended to indicate the direction of the reciprocal movement of the container relative to the housing, and of an indicating device cap member relative to a base member. The terms "top," "bottom," "upwardly" and "downwardly" are intended to indicate directions when viewing the inhalation devices as shown in the Figures, but with the understanding that the container is inverted such that the top surface thereof is located adjacent the bottom of the housing and vice versa. Moreover, it should be understood that a user can use the container and dispenser in any number of positions, including but not limited to the preferred upright position shown in FIGS. 4 and 12-14. The terms "connect," "connected," "couple," and "coupled," and equivalents thereof, refers to the connection of two components directly, or indirectly, i.e., by way of one or more intervening components.

As shown in FIG. 4, a cylindrical support block 212 having a well 214 is formed in a bottom portion 206 of the housing. An orifice 210 penetrates the support block to communicate with a bottom portion of the well. In one embodiment shown in FIGS. 4 and 14, a mouthpiece 208, intended for insertion into the mouth of a patient, forms an exhaust port 216 that communicates with the orifice and well. The mouthpiece 208 extends laterally from the housing so as to facilitate insertion of the mouthpiece into the mouth of the patient.

As shown in FIGS. 4 and 14, the container 12 is preferably cylindrical and has a hub 16 disposed on a top thereof. A valve stem 18 extends longitudinally from the hub. The valve stem extends coaxially from the container and is biased outwardly therefrom by a spring (not shown) mounted within the valve stem of the container. The container 12 is mounted in the housing by press fitting the valve stem 18 in the well 214 of the support block.

In a preferred embodiment, the container 12 is filled with a substance that is dispensed therefrom in specific metered doses by an actuation thereof effected by depressing or moving the valve stem 18 from an extended closed position to a depressed open position. Preferably the substance is a medicament, although it should be understood that the container may be used to hold a variety of non-medicinal substances, including, but not limited to, various liquids, foams or aerosols. In one preferred embodiment, the container is a pressurized, metered dose inhaler. A single metered dose is dispensed from the container by each reciprocal, longitudinal movement of the valve stem, or actuation of the container. It should also be understood that the valve system can be actuated by a variety of actuators, including, but not limited to, various pumps, levers, actuator boots, buttons and the like. In some embodiments, the container and valve system is breath-actuated, meaning they are actuated in response to the user inhaling, for example by inhaling through the mouthpiece. In such embodiments, the valve system can be actuated by an actuator moveable relative to the container and housing such that the container remains stationary relative to the housing.

In operation, the opening of the valve stem is effected by moving the container 12 reciprocally within the housing 200 along a longitudinal axis, defined by the valve stem and the reciprocal movement of the container, by depressing the bottom end 14 of the container relative to the housing so as to move the valve stem 18 to the open position as it is supported within the well by the support block. As the valve stem is moved to the open position, the container dispenses a metered dose of a substance through the well 214 and orifice 210. The substance, for example an aerosol and medicament, are then transmitted to the patient through an exhaust port 216 of the mouthpiece by 208 way of either a self-generated or assisted airflow.

In other delivery systems, the housing and holder for the container are attached to a component having a chamber with an output end. Examples of these kinds of delivery systems are shown for example in U.S. Pat. No. 5,012,803, issued May 7, 1991, and U.S. Pat. No. 4,460,412, issued Sep. 11, 1984, both of which are hereby incorporated herein by reference. (No license, expressed or implied, is intended to be granted to any patent by reason of the incorporation by reference herein). In these kinds of delivery systems, the component having the chamber can be adapted to receive the mouthpiece of the housing, or it can be integrally connected with a holder supporting the container. In either embodiment, the metered dose of medicament in aerosol is first dispensed from the container into the chamber, and thereafter inhaled by the patient.

In a preferred embodiment, the container 12 is intended to dispense a predetermined number of metered doses of a substance, such as a medicament, upon a corresponding number of predetermined actuations of the container. For example, conventional inhaler containers typically hold on the order of 100 to 200 metered doses. It should be understood, however, that the range of available doses could potentially vary from as few as one dose to as many as 500, or even more, depending, for example, on the capacity of the container, and/or the size of the metering dose valve. In operation, it can be important for the patient to be aware of the number of metered doses remaining in the container such that the patient is not caught unaware with an empty container when in need of the medicament.

Figure 31:
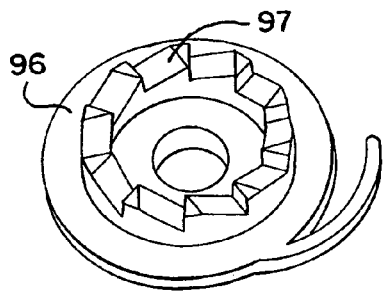
FIG. 31 is a bottom perspective view of the second indicator member.

Description of Indicating Devices Mounted to Bottom of Container:

Now generally referring to FIGS. 1–11, 18–33, 37 and 38, various dose indicating devices are shown. The indicating devices 10, 210 indicate the number of metered doses that have been dispensed from or remain in the container. The indicating device 10, 210 includes an indicating device housing comprised of a cap member 20, 220 disposed in a base member 40, 240. Alternatively, the base member can be disposed in the cap member. The base member 40, 240 is configured such that it can be mounted to the bottom of the container 12. In either embodiment, the base member 40, 240 includes a convex, or curved bottom portion 50, or floor, which is shaped to be received in and to mate with the bottom end 14 of the container, which has a concave or inwardly curved contour (see FIG. 4). Referring to FIGS. 4 and 31, the base member 40 is preferably connected to the bottom of the container, for example and without limitation by bonding with adhesive, double sided tape, or similar bonding agent. In one preferred embodiment, a label, or other wrapper, is wrapped around the side of the base and the container to join the base to the container. In one preferred embodiment, the outer circumferential surface of the base has substantially the same cross-sectional shape and contour as the outer circumferential surface of the container, which facilitates the joining thereof by way of a wrapper.

Figure 33:
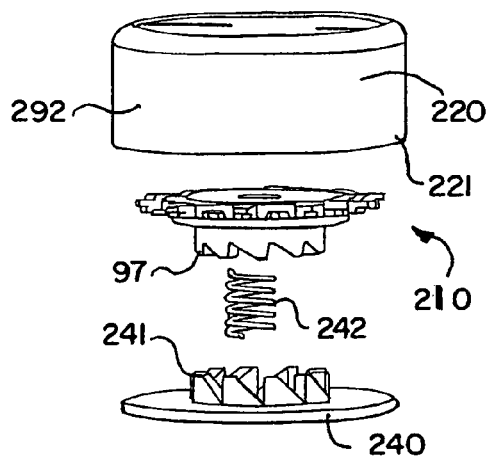
FIG. 33 is an exploded perspective view of an indicating device.
Figure 38:
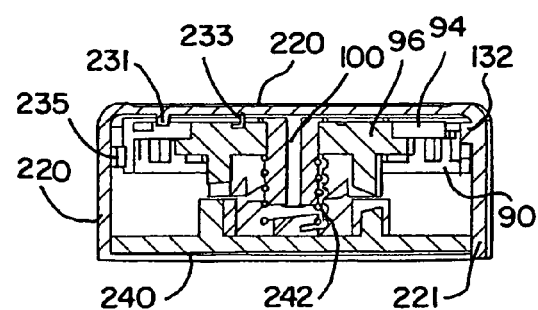
FIG. 38 is a side, cross-sectional view of the indicating device shown in FIG. 33.

As shown in the embodiment of FIGS. 1, 4, 8, and 9, a circumferential skirt member 194 extends upwardly from the base portion to form a cavity 196. Alternatively, the base member can also include a downwardly depending circumferential skirt that forms a recess or cavity, which is shaped to receive the bottom end of the container. In such an embodiment, the base member is fixedly mounted on the container by connecting one or more of the bottom portion or skirt to the container, for example and without limitation by bonding or by press fitting the container in the cavity so as to provide an interference fit between the container and the depending skirt. As shown in FIGS. 33 and 38, the base 240 does not have any skirt.

Although the disclosed container and indicating device, and in particular, the cap member and base member, are shown as preferably having a circular cross section, those skilled in the art should understand that the container and indicating device, including any adapter, can be configured in other shapes, including for example, but not limited to, rectangular, triangular, hexagonal, pentagonal, oval, etc. cross-sections.

As best shown in FIGS. 1, 2, 18, 21, 29, 33 and 38, the cap member 20, 220 has a top portion 52, 252 with a first viewing window 34, 234 formed therein. Preferably, the cap member 20, 220 is circular and the viewing window is formed in the top portion adjacent the middle of the cap (FIG. 2) or adjacent the outer periphery of the cap member (FIG. 18) so as to overlie indicia applied to one or more indicator members supported beneath the cap member. The viewing window can be configured in a number of various shapes. For example, the viewing window can be tapered, arcuate shaped, rectangular, obround, circular, etc. Of course, one of skill in the art should understand that any shape of window would work so long as the indicia is visible. The top of the cap member can be configured with a plurality of raised portions forming a grippable pattern for the user's thumb, or finger. In this way, the user can firmly press down on the cap member without slippage. One of skill in the art should recognize that other patterns or grippable surfaces, such as a knurled pattern, can be applied to the cap member to facilitate the use of the indicating device.

Referring to FIGS. 1, 3, 4, 18–31 and 33, the cap member 20, 220 comprises a circumferential skirt 192, 292 depending downwardly from the top portion 52, 252. The skirt preferably has a smaller diameter than the upwardly depending skirt of the base member, such that the cap member skirt nests within the upwardly extending skirt of the base member. Alternatively, the cap member can be configured with a skirt having a larger diameter than the skirt of the base member such that the base member skirt nests in the cap member skirt. In one embodiment, the cap member 20, 220 is moveably mounted to the base member 40, 240 by way of a snap fit.

In particular, as shown in FIGS. 1, 8, 9 and 11, the cap member 20 includes a plurality of engagement members 28 extending from an outer circumferential surface of the skirt. The cap member 20 is inserted axially within the recess or cavity 96 of the base member such that the engagement members 28, which have a tapered surface, slide past the rim 42 of the base member skirt until the engagement members are disposed in a plurality of pockets formed along the inner circumferential surface of the base member skirt to form a snap-lock fit. In particular, the upper surface of the engagement member engages an engagement surface defining the top of the pocket. In this way, the cap member is moveable with respect to the base member along an axial, or longitudinal, path. Alternatively, the rim of the base member can be curved slightly inward such that the engagement members engage the inwardly curved rim portion so as to prevent the cap member from being separated from the base member.

Referring to FIGS. 1, 4, 8, 20 and 31, the axial movement of the cap member 20, 220 relative to the base member 40, 240 is bounded or constrained by the engagement of the engagement members with the top of the base member pockets (or the base member rim) at a fully extended position and by engagement of a bottom rim 21, 221 of the cap member skirt with the upper surface of the bottom portion, or with the bottom of the container, at the bottom of the stroke as shown. One of skill in the art should understand that the engagement members can alternatively be formed on the base member skirt so as to engage pockets or openings, or a rim (or like protrusion), formed on the cap member skirt.

As shown in the embodiment of FIGS. 33 and 38, a spring 242 is disposed between the cap member and the base member. The spring can be formed as a compression spring, a washer, cantilever, torsion, leaf and/or tension springs, which bias the cap member upwardly into engagement with the base member. The springs can be made of metal or plastic.

As shown in FIGS. 3 and 9, the spring, or return mechanism acting between the cap member and base member, includes a plurality of resilient arm members 400 extending downwardly from the cap member. As the cap member is moved toward the base member, one or more of the arm members engages a ramped biasing surface 402 formed along the inside of the circumferential skirt 194 along an inner hub portion (not shown). The ramped biasing surface biases one or more of the resilient arm members outwardly as the cap member moves toward the base member. As shown in FIGS. 1 and 3, the arm members 400 are integrally formed in the circumferential skirt 192 of the cap member. The cap member further includes guide members 404 that are received in guides 406 formed in the base member, as shown in FIG. 9. In one embodiment, not shown, the guide members can be shaped to be received in only one of the guides, such that the cap member can be properly installed with the various indicator members connected thereto aligned with pawl formed in the base member. The guides 406 and guide members further act as key members to prevent the cap member from rotating relative to the base member. The guides can take any shape, for example rectangular or T-shaped.

The resilient arm member(s) 400 act as cantilever springs to bias the cap member away from the base member when the cap member is released by the user. One of skill in the art should understand that the resilient arm members can also be formed on the base member so as to engage a ramped surface formed on the cap member. In addition, it should be understood that one or more arm members and/or ramps may be used, with the size and shape of the arm member and/or ramp members being modified to provide more space between the cap member and base member.

Referring to the embodiment of FIGS. 1–11, a shaft 60 is non-rotatably mounted to the cap member. The ends 62 of the shaft are shaped, for example in a T-shape, to mate with a passageway formed in hubs 64 formed in the skirt 92 of the cap member so as to prevent relative rotation therebetween. In an alternative embodiment, the shaft is mounted to the base member.

An indicator member 72 includes a cylindrical display portion 66 and first and second ratchet gears disposed on each end of the display portion. The indicator member 72 is rotatably mounted on the shaft 60. The shaft has a helical groove 74 formed on an outer surface thereof. The pitch of the groove is determined by the number of factors, including the total count of actuations, the overall size of the device, the number of teeth on the ratchet gears, and the size of the display window. The indicator member 72 has a follower 76 extending radially inward from an inner surface 78 of an opening in the indicator member through which the shaft extends. The follower 76 is disposed in the groove 74. In an alternative embodiment, the groove is formed on the inner surface of the opening, and the follower extends radially outward from the shaft.

The display cylinder or portion 66 has dosage indicia 80 disposed on an outer surface thereof. In one preferred embodiment, the dosage indicia are configured as numerical indicia arranged in a helical pattern around the cylinder 66. In one preferred embodiment, the indicia 80 are arranged to count by ones, with the indicia corresponding to consecutive numbers. In other embodiments, the indicia are arranged to count by some other factor, e.g., by tens. One of skill in the art should understand that other dosage indicia indicating the number of doses remaining in or dispensed from the container would include, but not be limited to, various alpha-numerical characters, words, terms or phrases (such as "full" and "empty"), scales, grids, arrows, raised portions, indentations, color coding and segmentation, shading and like markings, or any combination thereof. For example, a segmented color grid displayed in the viewing window could turn from green, indicating a full container, to yellow, indicating an intermediate capacity, and finally to red, indicating an empty container. It should also be understood that the indicia can be formed integrally with the counter member, or applied thereto by means of paint, dye, etching, pad printing, hot stamping or adhesive labels. When using numerical indicia, the numbers can be arranged to go from 0 (or some beginning number) to the predetermined number of available doses such that a display of that number to the user indicates that the container should be replaced, or, conversely, to go from the starting predetermined number to 0 (or some ending number), which again indicates to the user that the container should be replaced.

In a preferred embodiment, the indicator member is made of acrylonitrile butadiene styrene ("ABS"), which is receptive to certain alternative processes of printing or applying the indicia, including pad printing and hot stamping. The cap member and base member are preferably made of a hard plastic material such as Acetel. In various preferred alternative embodiments, one or both of the base member and cap member can be made of polycarbonate.

Figure 10:
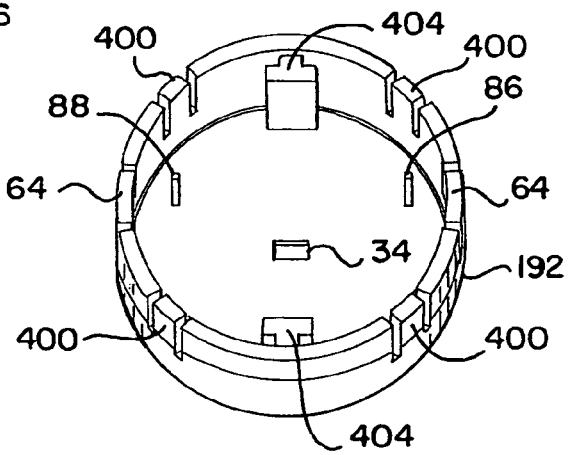
FIG. 10 is a bottom perspective view of a cap member.
Figure 11:
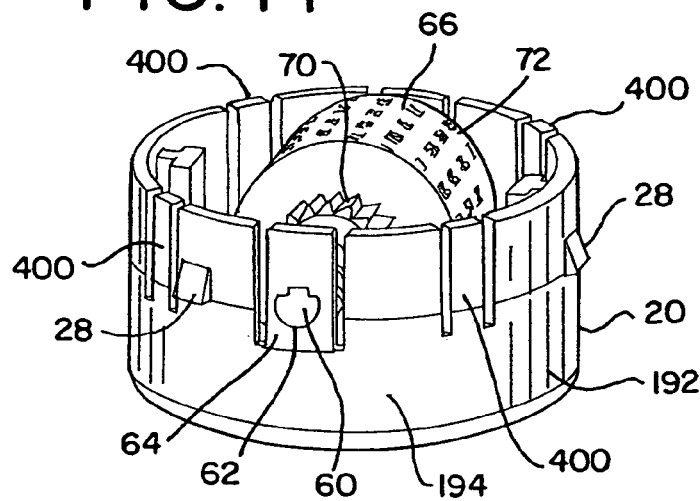
FIG. 11 is a side perspective view of a cap member with an indicator member mounted thereto.

Referring to FIGS. 8 and 9, first and second pawls 82, 84 extend longitudinally from the bottom of the base member. The pawls are laterally spaced apart and are positioned to selectively engage the first and second ratchet gears 68, 70 respectively depending on the position of the indicator member 72 relative to the shaft 60 along its axis. Referring to FIGS. 8 and 10, first and second non-return members 86, 88 extend longitudinally from the cap member 20 and are spaced apart such that they selectively engage the first and second ratchet gears 68, 70 respectively depending on the position of the indicator member relative to the shaft along its axis. In an alternative embodiment, the shaft and non-return members are disposed on the base member and the pawl members extend from the cap member. The ratchet gears 68, 70 each include a plurality of teeth 90 (preferably 10) formed around their respective peripheries. Each of the teeth includes an engagement surface and a tapered surface.

The base member 40 with the pawls 82, 84 are referred to and function as an actuator for the indicating device as the base is connected to and engaged by the container. Alternatively, the pawl members can be moveably secured to the cap member and extend through the base member to engage the top of the container, such that the axial movement of the cap member toward the container causes the pawls to move toward the ratchet gears and engage one of the teeth thereon as described below. When formed integrally with one or the other of the cap member and base member, the pawl members and non-return members are preferably made of the same materials as the respective cap member and base member.

Referring to FIGS. 18–21, 26–29 and 37–38, in another embodiment of the indicating device, first, second and third indicator members 94, 96, 98 are coaxially mounted on a shaft 100 extending longitudinally from the cap member 220. Alternatively, the shaft can extend from the base member. The shaft 100 defines a rotation axis that is parallel to the axial path of movement between the cap member and base member. First and second indicator members 94, 96 rings are visible in a first viewing window 234, as shown for example in U.S. Pat. No. 6,283,365, which is hereby incorporated herein by reference. The third indicator member is visible in a second viewing window 92, as shown in FIGS. 18 and 22–25.

Referring to FIGS. 20, 21, 23, 25 and 30, the third indicator member 98 has a semicircular top portion 102 with an upper surface having secondary dosage indicia 104 disposed thereon which is visible through the viewing window 92 formed in the top of the cap member. The indicia is formed in a helical or spiral pattern, and preferably includes a plurality of colors (e.g., green and red), for example two regions 106, 108, with one of the colors or regions 106 progressively filling more of the window, and the other color or region 108 progressively receding, as the indicator device is actuated.

The third indicator member 98 includes a plurality of longitudinally extending, resilient teeth 110 formed around the circumference of the top portion 102, with the teeth extending axially from a semicircular bar 112 attached at opposite ends to the top portion 102. The top of the teeth 110 are spaced from the top portion 102 such that the teeth are cantilevered from the bar 112 and can be resiliently biased radially inwardly.

Figure 21:
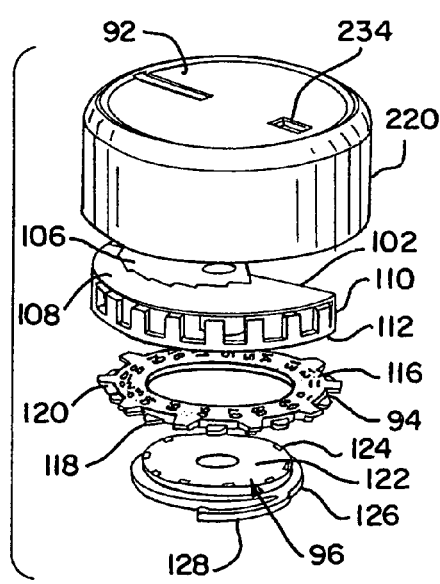
FIG. 21 is a top view of a portion of the indicating device shown in FIG. 19.
Figure 22:
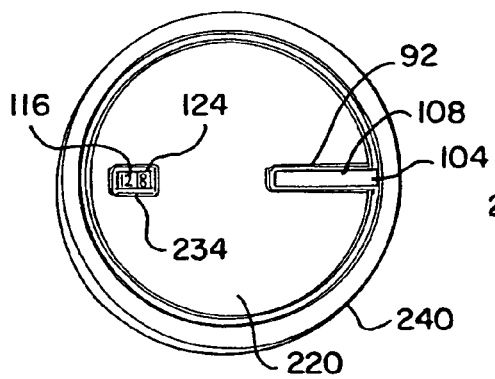
FIG. 22 is a top view of the indicating device shown in FIG. 18 with the indicator members positioned in an initial dose configuration.
Figure 26:
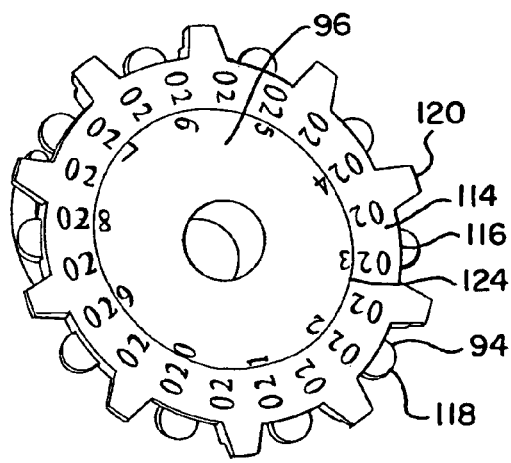
FIG. 26 is a top perspective view of the first and second indicator members.
Figure 27:
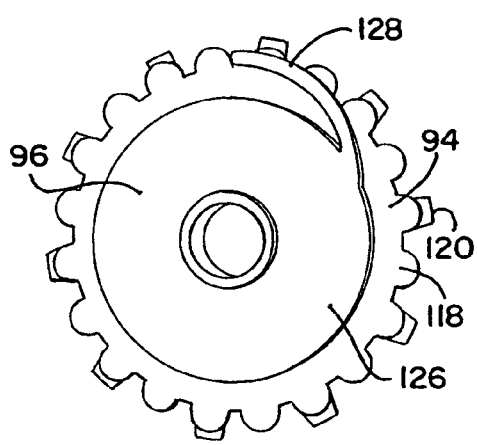
FIG. 27 is a bottom view of the first and second indicator members.

Referring to FIGS. 21 and 26, the first indicator member 94 has an upper surface 114 with primary indicia 116 disposed thereon and visible in a viewing window. The indicia 116 are preferably configured as numbers divisible by tens. The first indicator member 94 has a central opening formed therein. A plurality of driven teeth 118 extend radially outward from an outer circumferential periphery of the first indicator member 94. Underlying/overlying every other driven tooth 118 is a driving tooth 120 that extends radially outward from the circumferential periphery of the indicator member, with the plurality of driving teeth 120 being longer than and extending further radially outward than)the driven teeth 118. In one preferred embodiment, the first indicator member 94 includes twenty (20) driven teeth 118 and ten (10) driving teeth 120. The first indicator member has a plurality of indentations or detent openings 121 formed around the circumferential periphery thereof, with the number of indentations preferably corresponding to the number of drive teeth.

Figure 28:
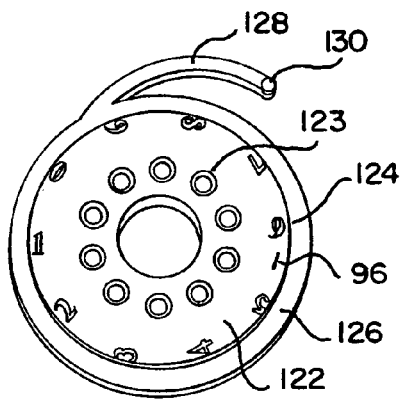
FIG. 28 is a top perspective view of the second indicator member.

Referring to FIGS. 21, 26 and 28, the second indicator member 96 has a central display portion 122 formed as a hub that is shaped to fit in the central opening of the first indicator member 94. The display portion 122 has a dosage indicia 124 (preferably numbers from 0 to 9) arranged around the outer circumference of the top of the display portion and adjacent to the numbers on the first indicator member. The second indicator member 96 includes a lower drive portion underlying the display portion. An advancement member 128, configured as a resilient arm, extends radially from the edge of the drive portion and has a circumferential curvature that follows the circumferential edge of the drive portion. The end of the advancement member includes an engagement portion 130 extending longitudinally upward from the arm so as to be aligned with or in the same plane with the driven teeth 118 of the first indicator member 94. The second indicator member 96 has a plurality of indentations or detent openings circumferentially formed around a central opening therein, with the number of indentations preferably corresponding to the number of indicia, for example 10.

Description of Operation of Various Embodiments of Indicating Devices Mounted to Bottom of Container:

In operation of the first embodiment of the indicating device, as shown in FIGS. 1–11, the user depresses the cap 20 member from a fully extended position toward the base member 40 such that the cap member bottoms out in the base member at the bottom of the stroke and such that the base member imparts an axial load on the container 12 until a metered dosage is dispensed therefrom. In a preferred embodiment, the biasing force of the return mechanism, such as the resilient arm members 400 which act as cantilever springs, is less than the biasing force of the spring located in the metering valve of the container, such that the cap member 20 first bottoms out in the base member with the container then being moved downwardly in the housing until a metered dose is dispensed.

Referring to FIGS. 3 and 4, the indicator member 72 is disposed adjacent one end of the shaft 60. As the cap member 20 is depressed toward the base member 40, the first pawl 82 selectively engages one of the teeth 90 on the first ratchet gear 68 and rotates the ratchet gear 68 and display cylinder 66. The tapered surface of one of the teeth formed on the first ratchet gear 68 simultaneously biases the first non-return member 86 outwardly until it selectively engages the next tooth near the bottom of the stroke. The non-return member 86 provides an audible click as it engages the next tooth. The user then releases the cap member 20 wherein after the spring 400, or similar return mechanism, biases the cap member 20 away from the base member 40 until the engagement member engages the base portion at the top of the stroke. When the cap member 20 is released by the user, the container 12 is biased upwardly within the housing along the longitudinal axis such that the valve stem 18 is moved to the closed position within the container. Simultaneously, as the cap member 20 is released and allowed to move away from the base member 40, the first pawl 82 is biased outwardly by one of the teeth on the first ratchet gear 68 as the non-return member 86 prevents a backwards rotation thereof so as to maintain a unidirectional rotation of the ratchet gear 68 and display portion 66. At the top of the stroke, the first pawl 82 is again placed in position for selective engagement with one of the teeth of the first ratchet gear 68. Again, the pawl provides an audible click as it engages the next tooth.

In summary, on the down stroke the non-return member makes a clicking sound as it slides over one or more ratchet teeth, while on the up stroke, the pawl member also makes a clicking sound as it slides over one or more ratchet teeth. In this way, the ratchet gear 68, and connected display cylinder 66, are advanced or rotated an incremental amount for every actuation of the container 12 and the attendant release of substance. The incremental amount is defined by and dependent on the number of teeth formed about the periphery of the ratchet gear 68. When formed with 10 teeth, as shown in the preferred embodiment, the ratchet wheel will make one full revolution for every 10 actuations of the indicator device 10 and container 12, or $\frac{1}{10}$th of a revolution for each actuation. One skilled in the art will appreciate that the ratchet gear 68 can be provided with various numbers of teeth formed about its periphery such that the more or less axial movements or actuations of the container are required to make one full rotation of the ratchet wheel.

Alternatively, the operation of the ratchet gear can be reversed. In this embodiment, the first pawl is biased outwardly by the tapered surface of one of the ratchet gear teeth on the downstroke. At the bottom of the stroke, the pawl is biased into engagement with one of the teeth. When the cap member is released by the patient, the spring, or equivalent return mechanism, biases the cap member upwardly within the base member along the longitudinal axis such that the pawl member engages one of the teeth and thereby rotates the ratchet wheel an incremental amount. In this embodiment, the non-return member maintains the rotational position of the ratchet wheel on the downstroke.

As the indicator member 72 is rotated by the first pawl member 82, the follower 76 moves or slides along the groove 74. Accordingly, the indicator member 72 is translated along, or moved relative to, the shaft 60 along the axis defined thereby. After a predetermined number of actuations, for example 60 corresponding to a container having approximately 120 doses, and as the indicator member 72 is moved from one position to another position (preferably proximate the middle of the cap member), the second ratchet gear 70 is brought into alignment with the second pawl 84 and the second non-return member 88, which act on the indicator member in the same way as described above with respect to the first pawl 82 and non-return member 86 relative to the first ratchet gear 68. In various embodiments, the first pawl and non-return member acts on the first ratchet gear simultaneously with the second pawl and non-return member acting on the second ratchet gear as the indicator member transitions therebetween. Alternatively, the second pawl and non-return member engage the second ratchet gear successively or consecutively with the engagement of the first pawl and non-return member with the first ratchet gear. In any case, at the indicator member must be engaged by one set of the pawls and non-return members.

The advancement or rotation of the indicator member 72 is stopped when the end of the indicator member travels to the end of the shaft and engages the skirt 192 or wall of the cap member. In one preferred embodiment, the indicator member and shaft are made of polycarbonate.

As the indicator member 72 is rotated and translated along the axis, the indicia 80 are progressively displayed in the viewing window 34 such that the user is apprised about the number of dosages of medicament remaining in the container, or dispensed therefrom.

Figure 32:
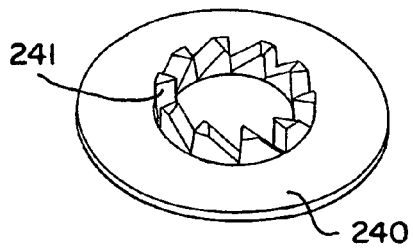

Referring to FIGS. 18–33 and 37–38, the second indicator member 96 is rotated in response to the axial movement of the cap member 220 relative to the base member as disclosed in U.S. Pat. No. 6,283,365, the entire disclosure of which is hereby incorporated by reference. In particular, as shown in FIGS. 31–33, teeth 241 formed on a base member 240 selectively engage teeth 97 on the second indicator member 96 to induce an incremental one-way rotation of the second indicator member. A spring 242 biases the cap member away from the base member.

Figure 23:
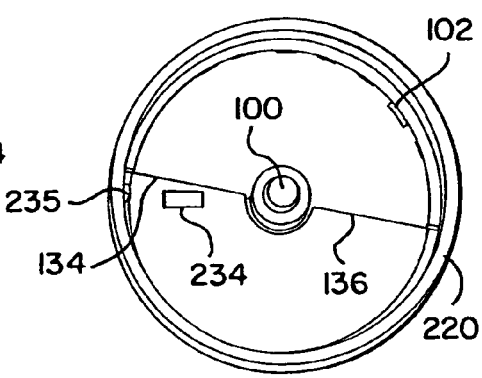
FIG. 23 is a bottom view of the third indicator member and cap member in the initial dose configuration.
Figure 24:
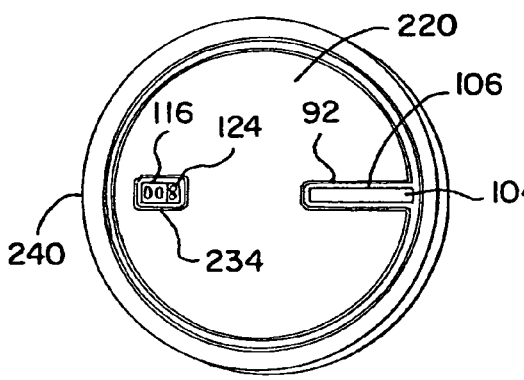
FIG. 24 is a top view of the indicating device shown in FIG. 18 with the indicator members positioned in a nearby empty configuration.
Figure 25:
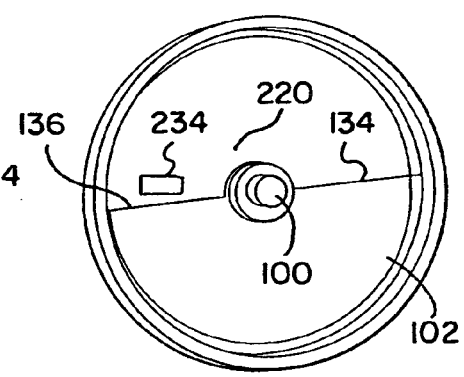
FIG. 25 is a bottom view of the third indicator member and cap member in the nearby empty configuration.
Figure 29:
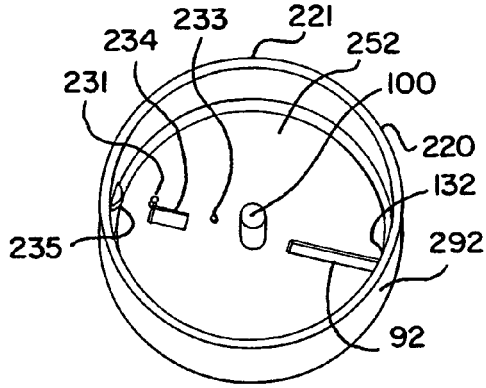
FIG. 29 is a bottom perspective view of the cap member.
Figure 30:
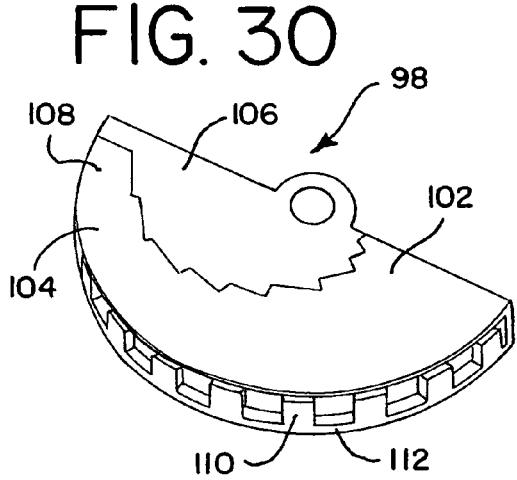
FIG. 30 is a top perspective view of the third indicator member.

As the second indicator member 96 completes a revolution, the advancement member 128 is biased radially inward by an engagement portion 235 shown in FIGS. 23 and 29, such that the engagement portion 130 at the end of the arm engages one of the driven teeth 118 on the first indicator member 94 and rotates the first indicator member an incremental amount after every revolution of the second indicator member. In this way, the first and second indicator members provide the user with indicia as to the number of dosages of substance remaining in or dispensed from the container. The indicia 116, 124 on the indicia first and second indicator members provides the user with indicia about the number of dosages of substance dispensed from or remaining in the container.

Detents 231, 233, configured for example as protuberances, formed in the top of the cap member 220 selectively engage the indentations 121, 123 formed in the first and second indicator members 94, 96 respectively, so as to index the first and second indicator members and to thereby prevent rotation of the first and second indicator members between actuations of the container.

As the first indicator member 94 is rotated, one of the driving teeth 120 selectively engages one of the teeth 110 on the third indicator member 98, as the respective tooth 110 is biased inwardly by an engagement portion 132 formed on the cap. The teeth 110 are preferably circumferentially spaced the same amount as the driven teeth 118 on the first indicator member 94, which is one half the distance between the driving teeth 120. Accordingly, the first indicator member 94 rotates two incremental amounts for every one incremental advancement of the third indicator member 98. The teeth 110 on the third indicator member 98 are successively engaged by the engagement member 132 and biased radially inward upon each advancement of the third indicator member 98 so as to be positioned for engagement with the next driving tooth 120 as it is rotated into engagement therewith. As shown in FIGS. 22–25, the third indicator member 98 will rotate approximately 180° as the first indicator member rotates approximately 360°. In an initial position (FIGS. 22 and 23), the third indicator member 98 has first edge 134 positioned adjacent to but not blocking the viewing window 238. In an end position (FIGS. 24 and 25), a second edge 136 is positioned adjacent to but not blocking an opposite side of the window 234.

Various indicating devices and components thereof are disclosed in U.S. Pat. Nos. 6,082,358, 6,142,339, 6,161,724, 6,283,365, 6,435,372, 6,561,384, 6,336,453 and 6,328,037, and U.S. Provisional Application Ser. No. 60/515,316, entitled Indicating Device With Warning Dosage Indicator and filed Oct. 28, 2003, all of which are hereby incorporated herein by reference in their entirety.

Description of Indicating Device Disposed in Dispenser Housing and Operator Thereof:

Now referring to FIGS. 12–17, an aerosol dispenser is shown as including a housing 200, a container 12 mounted therein as described above and an indicator assembly 138. The assembly includes an indicator member 140 rotatably disposed in the cavity 202 of the housing. The indicator member includes a longitudinally extending wall 142, preferably formed as a portion of a cylinder and having a circumferential outer suface with dosage indicia 114 applied thereto. Preferably, the wall 112 has a half cylindrical cross-section and is shaped and dimensioned to surround at least a portion of the container 12. The dispenser housing 200 has an elongated, longitudinally extending viewing window 146, formed as a slot. The indicia 144 are visible through the 146.

A driven gear 148 is formed along a bottom wall 150 that extends radially inward from the side wall. The gear includes a plurality of teeth that extend longitudinally from the bottom wall.

Figure 15:
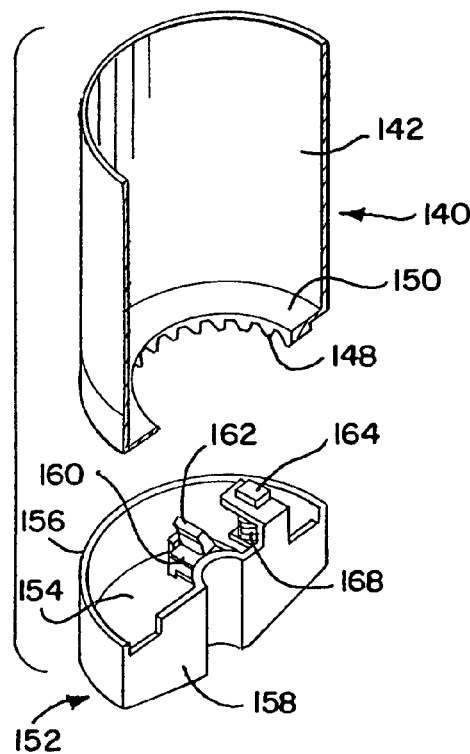
FIG. 15 is a top exploded perspective view of the second embodiment of the dose indicating device.
Figure 16:
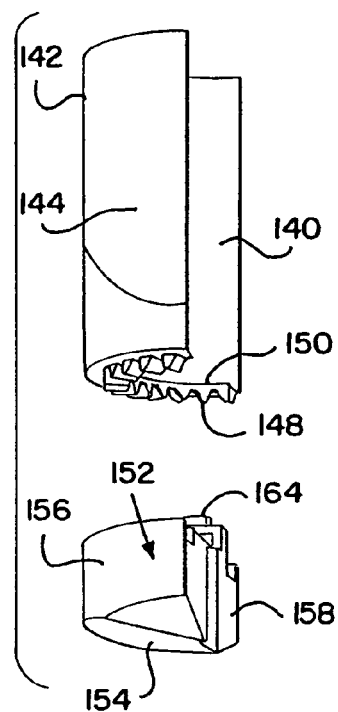
FIG. 16 is a side view of the second embodiment of the dose indicating device.
Figure 17:
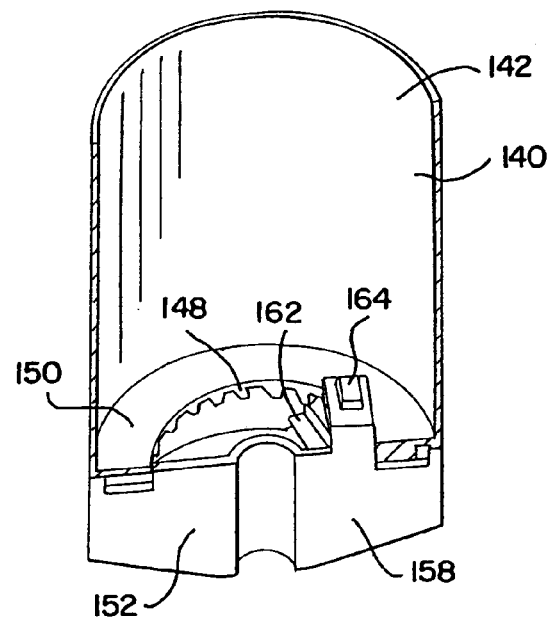
FIG. 17 is a top perspective view of the second embodiment of the dose indicating device.
Figure 18:
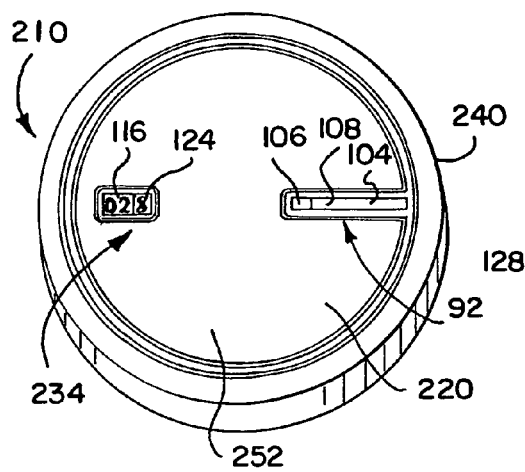
FIG. 18 is a top perspective view of a third embodiment of a dose indicating device.
Figure 19:
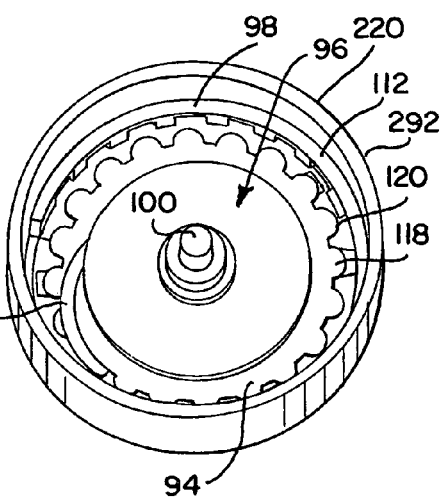
FIG. 19 is a bottom perspective view of a cap member with first, second and third indicator members disposed therein.
Figure 20:
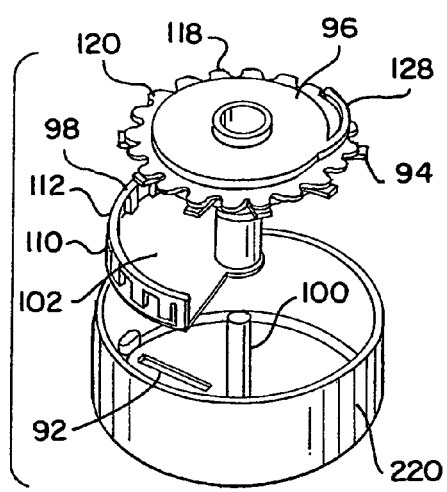
FIG. 20 is a bottom, exploded perspective view of a portion of the indicating device shown in FIG. 19.
Figure 34:
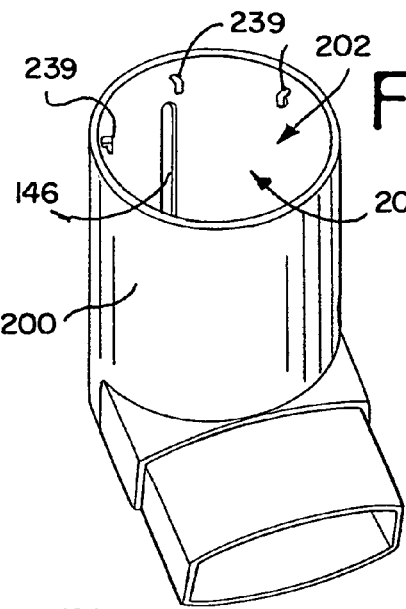
FIG. 34 is a top perspective view of an embodiment of a dispenser housing.
Figure 36:
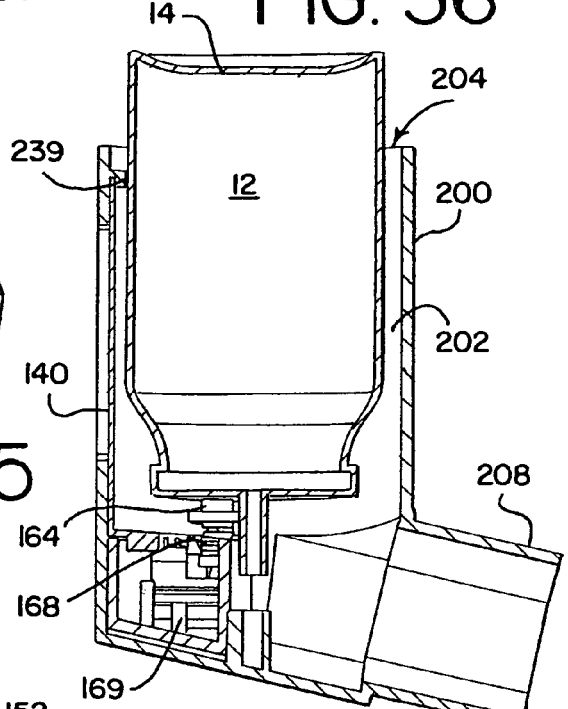
FIG. 36 is a partial side, cross-sectional view of an assembled dispenser housing, container and second embodiment of an indicating device.
Figure 35:
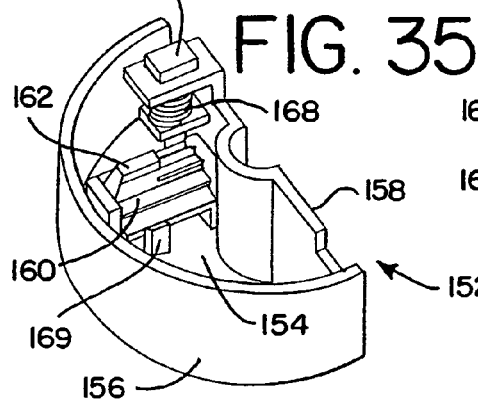
FIG. 35 is a top perspective view of a portion of the second embodiment of the indicating device.
Figure 37:
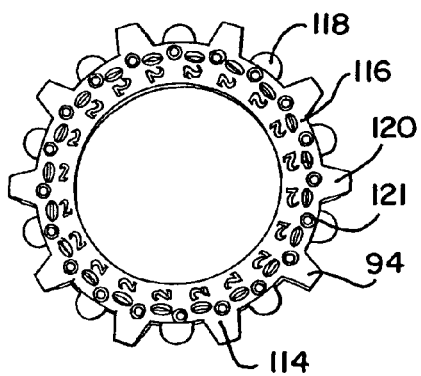
FIG. 37 is a top view of the first indicator member.

Referring to FIGS. 13, 15 and 17, a housing 152 includes a bottom 154, an outer wall 156 and an inner wall 158 having a channel that is shaped to be disposed around the support block. The housing 152 is shaped to be disposed in the bottom of the cavity 202 of the dispenser housing 200 behind and surrounding at least a portion of the support block. The outer wall 156 has a top surface that supports a bottom surface of the bottom wall 150 of the indicator member. As shown in FIGS. 34 and 36, the dispenser housing 200 has a plurality of tabs or hooks 239 that engage the top edge of the indicator member wall 140, which retain the indicator member in the dispenser housing. A drive gear 160 is rotatably mounted in the housing 152 and include a plurality of teeth 166. A drive member 162 or portion extends radially outwardly from the drive gear. The housing 152 can be secured to the housing 200 by snap-fit, for example with lugs, welding, bonding (adhesives, etc.), mechanical fasteners and other types of connection.

Referring to FIGS. 13, 15, 17, 35 and 36, an actuator 164 or pawl is moveably mounted to the housing 152 in an overlying relationship with the teeth 166 on the drive gear 160. A spring 168 biases the actuator away from selective engagement with the drive gear. A non-return member 169 selectively engages at least one of the teeth 166 of the drive gear 160 to prevent rotation thereof in one direction.

In operation, the user moves the container 12 relative to the housing 152, 200 so as to dispense a dose of substance. As the container is moved downwardly, the bottom of the container engages the top of the actuator 164 and moves the actuator longitudinally against the biasing force of the spring 168 until an opposite engagement end, or pawl, selectively engages at least one tooth 166 of the drive gear 160 and rotates the drive gear an incremental amount. It should be understood that the actuator and non-return members can be configured such that the drive gear is rotated on the upstroke of the actuator (and the container relative to the housing) and is maintained in position by the non-return member upon the downstroke of the actuator (and container relative to the housing).

Upon every complete rotation (360°) of the drive gear 160, the drive member 162 is brought into selective engagement with at least one of the teeth formed on the indicator member gear 148. As the drive gear 160 rotates the gear 148, the indicator member 140 is rotated about the longitudinal axis an incremental amount. It should be understood that the drive gear can be provided with more than one drive member, or varying numbers of teeth, such that the drive gear moves the indicator member more or less times respectively as desired. As the indicator member 140 is rotated, the indicia 144 visible through the viewing window 146 are changed so as to provide indicia to the user about the number of dosages of substance remaining in or dispensed from the container. In one preferred embodiment, the indicia are configured as a varying color pattern that gradually turns from green to red as the container is emptied.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. An indicating device suitable for indicating the number of metered dosages that have been dispensed from or remain in a container, said indicating device comprising:
   a base member adapted to be mounted to the container;
   a cap member moveably connected to said base member, said cap member reciprocally moveable relative to said base member along an axial path;
   a shaft mounted to one of said cap member and said base member, said shaft defining an axis; and
   an indicator member rotatably mounted on said shaft, said indicator member rotatable about said shaft in at least a first direction;
   wherein one of said shaft and said indicator member comprise a helical groove and the other of said shaft and said indicator member comprises a follower disposed in said groove, wherein said indicator member is translatably moveable relative to said shaft along said axis as said indicator member is rotated in said first direction about said axis.

2. An indicating device suitable for indicating the number of metered dosages that have been dispensed from or remain in a container, said indicating device comprising:
   a base member adapted to be mounted to the container;
   a cap member moveably connected to said base member, said cap member moveable relative to said base member along an axial path;
   a shaft mounted to one of said cap member and said base member, said shaft defining an axis; and
   an indicator member rotatably mounted on said shaft, said indicator member rotatable about said shaft in at least a first direction;
   wherein one of said shaft and said indicator member comprise a helical groove and the other of said shaft and said indicator member comprises a follower disposed in said groove, wherein said indicator member is moveable relative to said shaft along said axis as said indicator member is rotated in said first direction; and wherein the other of said cap member and said base member comprises at least one pawl and wherein said indicator member comprises a ratchet gear, wherein said at least one pawl selectively engages said ratchet gear and rotates said indicator member an incremental amount in said first direction as said cap member is moved relative to said base member along said axial path.

3. The indicating device of claim 2 further comprising at least one non-return member extending from said one of said cap member and said base member, wherein said at least one non-return member selectively engages said ratchet gear and prevents said indicator member from rotating in a second direction opposite said first direction.

4. The indicating device of claim 2 wherein said indicator member comprises a cylinder having an outer circumferential surface with dosage indicia applied thereto.

5. The indicating device of claim 4 wherein said dosage indicia is arranged in a helical pattern.

6. The indicating device of claim 5 wherein said dosage indicia comprise numbers.

7. The indicating device of claim 6 wherein said dosage indicia comprise colors.

8. The indicator device of claim 4 wherein said indicator member is moveable along said shaft between at least first and second positions, said indicator member comprises at least first and second ratchet gears positioned at opposite ends of said cylinder, and wherein said other of said cap member and said base member comprises at least first and second spaced apart pawl members, wherein said first pawl member is positioned to selectively engage said first ratchet gear when said cylinder is in a first position, and wherein said second pawl member is positioned to selectively engage said second ratchet gear when said cylinder is moved to said second position.

9. The indicating device of claim 4 wherein one of said cap member and said base member comprises viewing window, wherein said dosage indicia are visible through said viewing window.

10. The indicating device of claim 2 wherein said shaft is non-rotatably mounted to said cap member and said base member comprises said at least one pawl.

11. A method for indicating the number of metered dosages of substance dispensed from or remaining in a container comprising:

providing a base member adapted to be mounted to the container, a cap member moveably connected to said base member, a shaft mounted to one of said cap member and said base member, said shaft defining an axis, and an indicator member rotatably mounted on said shaft, said indicator member rotatable about said shaft in at least a first direction, wherein one of said shaft and said indicator member comprise a helical groove and the other of said shaft and said indicator member comprises a follower disposed in said groove;

reciprocally moving said cap member relative to said base member along an axial path;

rotating said indicator member about said shaft in a first direction;

moving said follower in said groove; and translating said indicator member relative to said shaft along said axis while said rotating said indicator member about said shaft.

12. A method for indicating the number of metered dosages of substance dispensed from or remaining in a container comprising:

providing a base member adapted to be mounted to the container, a cap member moveably connected to said base member, a shaft mounted to one of said cap member and said base member, said shaft defining an axis, and an indicator member rotatably mounted on said shaft, said indicator member rotatable about said shaft in at least a first direction, wherein one of said shaft and said indicator member comprise a helical groove and the other of said shaft and said indicator member comprises a follower disposed in said groove;

moving said cap member relative to said base member along an axial path;

rotating said indicator member about said shaft in a first direction;

moving said follower in said groove; and moving said indicator member relative to said shaft along said axis;

wherein the other of said cap member and said base member comprises at least one pawl and wherein said indicator member comprises a ratchet gear, and wherein said rotating said indicator member comprises selectively engaging said ratchet gear with said at least one pawl.

13. The method of claim 12 further comprising providing at least one non-return member extending from said one of said cap member and said base member, and selectively engaging said ratchet gear with said at least one non-return member and to thereby prevent said indicator member from rotating in a second direction opposite said first direction.

14. The method of claim 13 wherein said indicator member comprises a cylinder having an outer circumferential surface with dosage indicia applied thereto.

15. The method of claim 14 wherein said moving said indicator member relative to said shaft along said axis comprises moving said indicator member along said shaft between at least first and second positions, and wherein said indicator member comprises at least first and second ratchet gears positioned at opposite ends of said cylinder, and wherein said other of said cap member and said base member comprises at least first and second spaced apart pawl members, wherein said rotating said indicator member when in said first position comprises selectively engaging said ratchet gear with said first pawl member, and wherein rotating said indicator member when in said second position comprises selectively engaging said ratchet gear with said second pawl member.

16. A dispensing device including an indicating device suitable for indicating the number of metered dosages that have been dispensed from or remain in a container, said dispensing device comprising:

a housing having a longitudinally extending cavity shaped to receive the container;

said container comprising first and second longitudinally spaced ends;

a valve stem extending longitudinally away from said first end of said container in a direction opposite said second end, said valve stem coupled to said housing;

an indicator member disposed in said cavity and having a longitudinally extending wall surrounding at least a portion of the container between said first and second ends of said container, said indicator member rotatably mounted within said housing and rotatable relative thereto about a longitudinal axis, said indicator member comprising a driven gear;

a drive gear disposed in said housing and comprising a drive portion selectively engaged with said driven gear; and an actuator adapted to move with the container, said actuator selectively engaged with said drive gear.

17. The dispensing device of claim 16 wherein said wall defines at least a part of a cylinder.

18. The dispensing device of claim 16 wherein said housing comprises a first housing and further comprising a second housing disposed in a bottom of said first housing, wherein said drive gear and said actuator are disposed at least in part in said second housing, wherein said second housing is positioned adjacent an end of said indicator member.

19. The dispensing device of claim 16 wherein said housing has a longitudinally extending viewing window, wherein an outer surface of said wall of said indicator member has dosage indicia disposed thereon and visible through said viewing window.

20. An indicating device suitable for indicating the number of metered dosages of a substance that have been dispensed from or remain in a container, said indicating device comprising:

a base member adapted to be mounted to the container;

a cap member moveably connected to said base member, said cap member reciprocally moveable relative to said base member along an axial path;

a first indicator member comprising first primary dosage indicia and a second indicator member comprising second primary dosage indicia, wherein said first and second primary dosage indicia are adapted to indicate the number of dosages of substance that have been dispensed from or remain in the container, said first indicator member comprising a plurality of first driven teeth and a plurality of driving teeth, said second indicator member comprising a first advancement member selectively engaged with at least one of said plurality of said first driven teeth;

a third indicator member comprising secondary dosage indicia, wherein said secondary dosage indicia is adapted to indicate that less than a minimum predetermined number of dosages of substance remain in the container, said third indicator member comprising a plurality of second driven teeth;

wherein said first, second and third indicator members are rotatably mounted in one of said cap member and said base member, and wherein said one of said cap member and said base member comprises a first engagement member selectively engaged with and biasing at least one of said plurality of second driven teeth into engagement with at least one of said plurality of said driving teeth on said first indicator member, and wherein said one of said cap member and said base member comprises a second engagement member selectively engaged with and biasing said first advancement member into selective engagement with said at least one of said plurality of said first driven teeth.

21. The indicating device of claim 20 wherein said first, second and third indicator members are rotatably mounted on said cap member.

22. The indicating device of claim 20 wherein said first and second primary dosage indicia comprise numbers and wherein said secondary dosage indicia comprises color.

* * * * *